United States Patent [19]
Schweikard et al.

[11] Patent Number: 6,144,875
[45] Date of Patent: Nov. 7, 2000

[54] APPARATUS AND METHOD FOR COMPENSATING FOR RESPIRATORY AND PATIENT MOTION DURING TREATMENT

[75] Inventors: Achim Schweikard, Hamburg, Germany; John R. Adler, Stanford, Calif.

[73] Assignee: Accuray Incorporated, Sunnyvale, Calif.

[21] Appl. No.: 09/270,404

[22] Filed: Mar. 16, 1999

[51] Int. Cl.[7] .................................................. A61B 6/00
[52] U.S. Cl. ...................... 600/427; 606/130; 600/429; 600/439; 378/69
[58] Field of Search .................................. 600/425, 426, 600/427, 437, 439, 429, 428; 606/130; 378/69, 205; 356/375

[56] References Cited

U.S. PATENT DOCUMENTS

| | | | |
|---|---|---|---|
| 4,583,538 | 4/1986 | Onik et al. ............................... | 128/303 |
| 5,447,154 | 9/1995 | Cinquin et al. ........................ | 128/653.1 |
| 5,537,452 | 7/1996 | Shepherd et al. ......................... | 378/65 |
| 5,588,430 | 12/1996 | Bova et al. ............................ | 128/653.1 |
| 5,622,187 | 4/1997 | Carol ......................................... | 128/897 |
| 5,727,554 | 3/1998 | Kalend et al. ......................... | 128/653.1 |
| 5,971,997 | 10/1999 | Guthrie et al. ............................ | 606/130 |

Primary Examiner—Marvin M. Lateef
Assistant Examiner—Eleni Mantis Mercader
Attorney, Agent, or Firm—Gray Cary et al.

[57] ABSTRACT

An apparatus and method for performing treatment on an internal target region while compensating for breathing and other motion of the patient is provided in which the apparatus comprises a first imaging device for periodically generating positional data about the internal target region and a second imaging device for continuously generating positional data about one or more external markers adapted to be attached to the patient's body or any external sensor such as a device for measuring air flow. The apparatus further comprises a processor that receives the positional data about the internal target region and the external markers in order to generate a correspondence between the position of the internal target region and the external markers and a treatment device that directs the treatment towards the position of the target region of the patient based on the positional data of the external markers.

42 Claims, 13 Drawing Sheets

SYSTEM BLOCK DIAGRAM

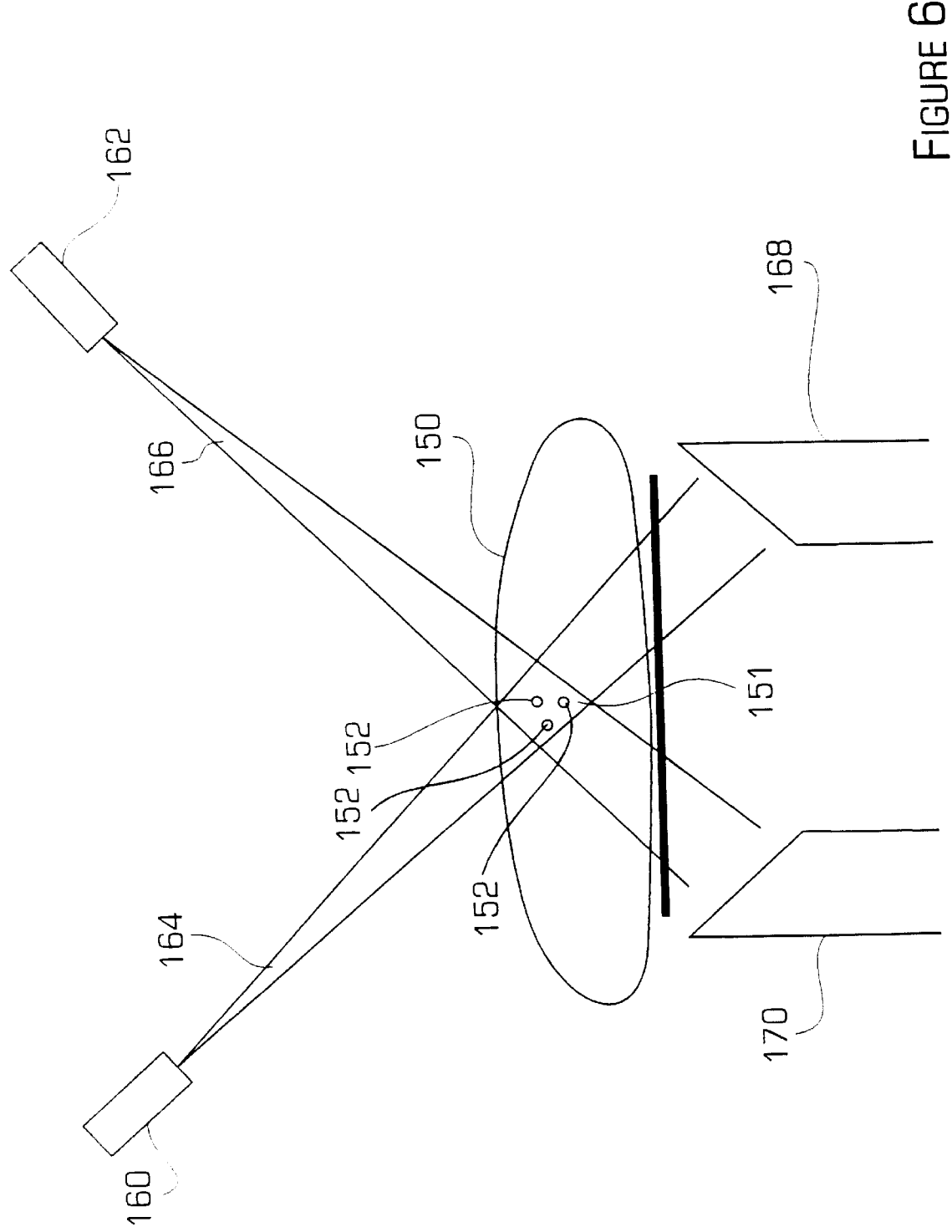

APPARATUS AND METHOD FOR COMPENSATING FOR RESPIRATORY AND PATIENT MOTION DURING TREATMENT

BACKGROUND OF THE INVENTION

This invention relates generally to an apparatus for improving the accuracy and efficacy of surgical treatments and more particularly to locating a target region to be treated and tracking the motion of the target region due to respiratory and other patient motions during the treatment.

Various different treatments may accurately track the motion of a target region in order to apply the treatment to the target region. In radiation therapy and radiosurgery, for example, a tumor may be destroyed by a beam of ionizing radiation which kills the cells in the tumor. The problem is that the tumor may move during treatment, especially due to the breathing motion of the patient. Such respiratory motion is difficult to track using external sensors, since the extent and direction of the internal breathing motion of the patient cannot be seen with traditional imaging devices. The breathing and other motion of the patient means that it is more difficult to focus the radiation on the tumor which means that the treatment may be less effective and healthy tissue may be unnecessarily damaged.

To allow for adequate distribution of radiation dosage to the tumor, the radiation beam is typically moved during the treatment. For conventional systems, the beam is moved along circular arcs in space. The goal is to give a very high dose of radiation to the tumor only, while protecting surrounding healthy tissue as much as possible. Although this radio-surgery technique has been applied with dramatic success to brain tumors, the extension of this technique to tumors outside the head or neck areas remains difficult. The main reason for this difficulty has been the problem of accurate target localization (i.e., accurate tracking of the motion of the target). In particular, breathing motion and other organ and patient motion make it difficult to track the target tumor with high precision so that it is difficult to achieve the goal of providing a high dose of radiation to the tumor while protecting surrounding healthy tissue. Furthermore, conventional systems can only move the radiation beam along circular arcs in space so that irregular breathing motions cannot be easily followed since these breathing motions may not occur along the axis of the circular arcs traced by the radiation beam.

Another radiosurgery technique uses a mechanical robotic device having six degrees of freedom that targets a radiation beam as disclosed in U.S. Pat. No. 5,207,223 to Adler. The robotic device permits the radiation treatment beam to be accurately positioned to apply the treatment beam directed to the target region. A method for neurosurgical navigation is disclosed in U.S. Pat. No. 5,769,861. This method relates to finding fixed targets, such as a brain tumor, but does not address tracking the motion of a target organ, such as lung due to breathing, with respect to the skin surface, or tracking the motion of internal abdominal organs with respect to externally visible motion. A fiducial that may be implanted into the human body so that it is detectable by an imaging system is also disclosed in which the fiducial implant is implanted into the bone or organs of the human body. This fiducial implant permits internal structures of the human body to be analyzed, but does not attempt to compensate for motion of a target organ which moves throughout the respiratory cycle. Thus, it is desirable to provide an apparatus and method for compensating for respiratory and other patent motion in radiation treatment and it is to this end that the present invention is directed.

SUMMARY OF THE INVENTION

In accordance with the invention, an apparatus and method for compensating for breathing and other motion of a patient is provided which combines internal markers placed on the target organ with one or more external sensors to accurately track the position and motion of a moving target region, such as an internal organ. In particular, the position of the internal markers, determined periodically by x-rays, may be combined with the position of the external sensors. The internal markers may be imaged only periodically since an invasive technology, such as x-rays, are needed to image the internal markers. The external continuous or real-time sensor, which may be an external marker, determines external motion during treatment. Thus, the position of the target organ may be precisely determined by the position of the internal markers when the internal markers are periodically imaged and may be determined based on the external sensor data while the internal markers are not being imaged. The position and motion of the internal markers relative to the external sensors are determined so that the position of the internal markers and therefore the target organ may be accurately determined by the position of the external sensor. Thus, the position of the target organ may be accurately determined throughout the medical procedure being performed.

The internal markers may be imaged using a number of different imaging technologies, including x-rays, nuclear magnetic resonance, ultrasound and other technologies which permit markers inside of the body of the patient to be imaged. Alternatively, three dimensional ultrasound images may be used to establish the location of the internal target region in lieu of discrete fiducials. The position of the external sensor may also be determined using a number of different technologies including infrared imaging, visual imaging, magnetic localization, the measurement of respiration, and any other type of technology which permits the external markers to be imaged. In addition to using external sensors (i.e., external fiducials may not be used), it is also possible to visually image a body surface which is then correlated to the internal fiducials.

Thus, in accordance with the invention, an apparatus for performing treatment on an internal target region while measuring and in some cases compensating for breathing and other motion of the patient is provided. The apparatus comprises a first imaging device for periodically generating positional data about the internal target region and a second imaging device for continuously generating positional data about one or more external markers attached to the patient's body. The apparatus further comprises a processor that receives the positional data about the internal target region and the external sensor readings/measurements in order to generate a correspondence between the position of the internal target region and the external marker or sensor readings and a treatment device that directs the treatment towards the position of the target region of the patient based on the positional data of the external markers or sensor readings. An apparatus for compensating for motion of a patent during treatment is also disclosed as well as a method for compensating for motion of the patient.

BRIEF DESCRIPTION OF THE DRAWINGS

FIG. 6 is a diagram illustrating one or more internal markers attached to the target organ being imaged by x-ray devices;

DETAILED DESCRIPTION OF A PREFERRED EMBODIMENT

Figure 1:
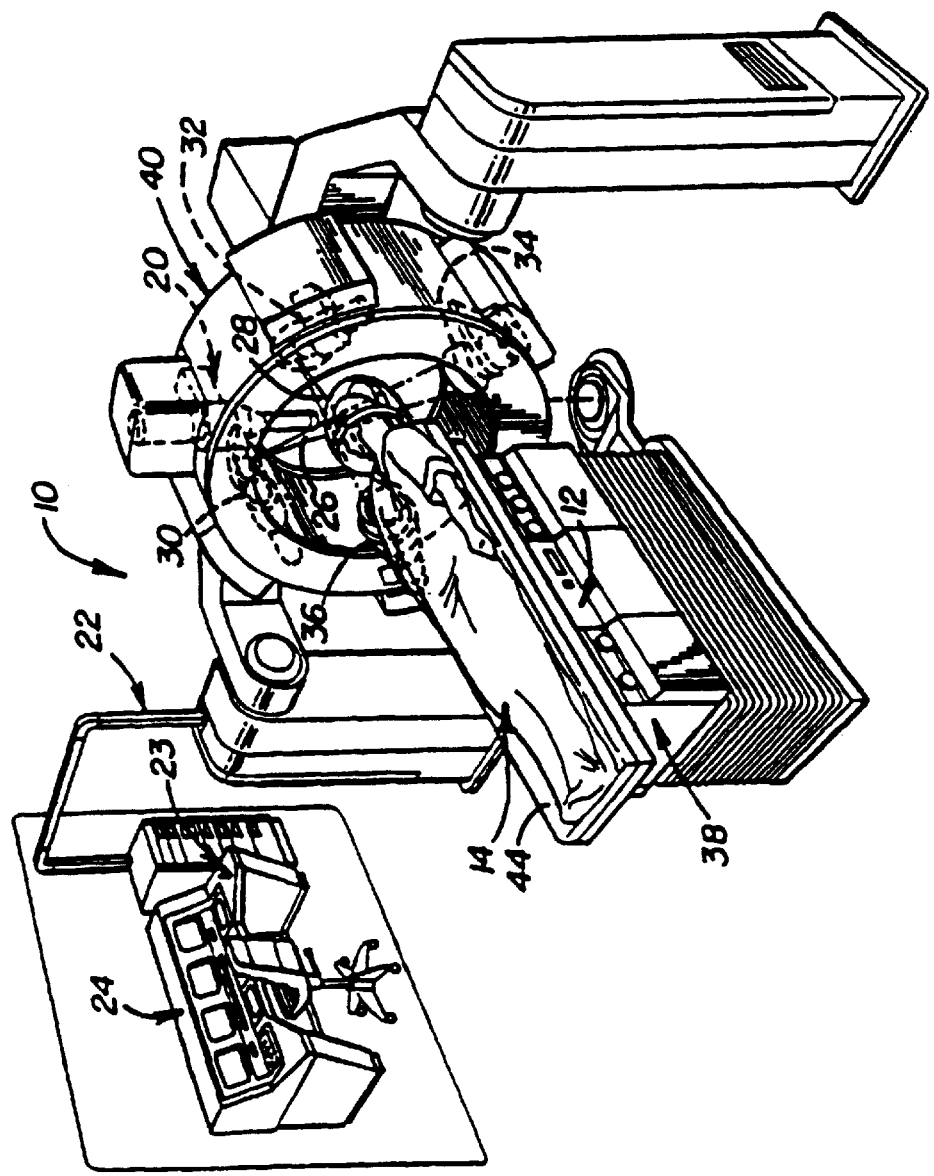
FIG. 1 is a diagram illustrating a conventional radiation treatment device.

The invention is particularly applicable to an apparatus and method for compensating for breathing and other patient motion during radiation treatment (radiosurgery) and it is in this context that the invention will be described. It will be appreciated, however, that the apparatus and method in accordance with the invention has greater utility, such as to other types of medical procedures with other types of medical instruments, such as positioning biopsy needles, ablative, ultrasound or other focused energy treatments, or positioning a laser beam for laser beam treatment. Prior to describing the invention, a typical radiosurgery device will be described to provide a better understanding of the invention.

FIGS. 1–4 are diagram illustrating an example of a stereotaxic radiation treatment device 10. The radiation treatment device 10 may include a data processor 12, such as a microprocessor, and a disc or tape storage unit 13 (shown in FIG. 4) which may store a three dimensional image of a patient 14. The three dimensional image may be loaded into the data processor, if not already there, to compare the three dimensional image to images generated during the surgical procedure. The three dimensional image may be generated by various conventional techniques such as computer aided tomography (CAT) scan or magnetic resonance imaging (MR). The radiation treatment device 10 may also include a beaming apparatus 20 which, when activated, emits a collimated surgical ionizing beam directed at a target region 18 (shown in FIG. 2). The collimated surgical ionizing beam may have sufficient strength to cause the target region to become necrotic. A variety of different beaming apparatus may be used which generate an ionizing radiation or heavy particle beam such as a linear accelerator and preferably an x-ray linear accelerator. Such an x-ray beaming apparatus is commercially available. The beaming apparatus may be activated by the operator throwing a switch 23 at a control console 24 connected to the beaming apparatus 20 by a cable 22.

Figure 2:
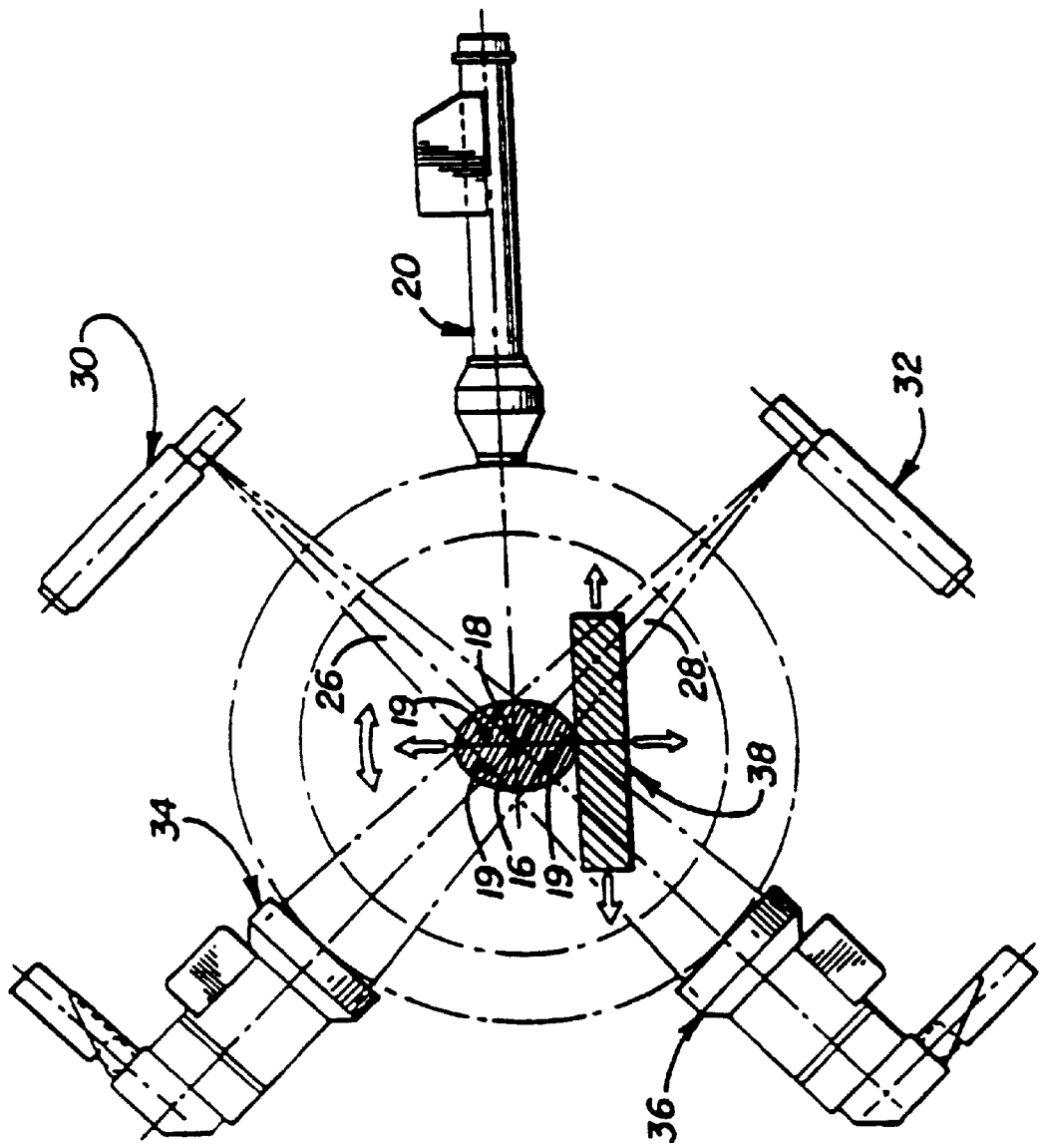
FIG. 2 is a diagram illustrating more details of the radiation treatment device.

The radiation treatment device 10 may also include an apparatus for passing a first diagnostic beam 26 and a second diagnostic beam 28 through the region previously imaged by the three-dimensional image. The diagnostic beams are positioned at a predetermined non-zero angle with respect to each other, such as being orthogonal as shown in FIG. 2. The diagnostic beams may be generated by a first x-ray generator 30 and a second x-ray generator 32, respectively. A first and second image receiver 34, 36 may receive the diagnostic beams 26, 28 to generate an image from the diagnostic beams which is fed into the microprocessor 12 (as shown in FIG. 4) so that the diagnostic images may be compared to the three-dimensional image.

Figure 3:
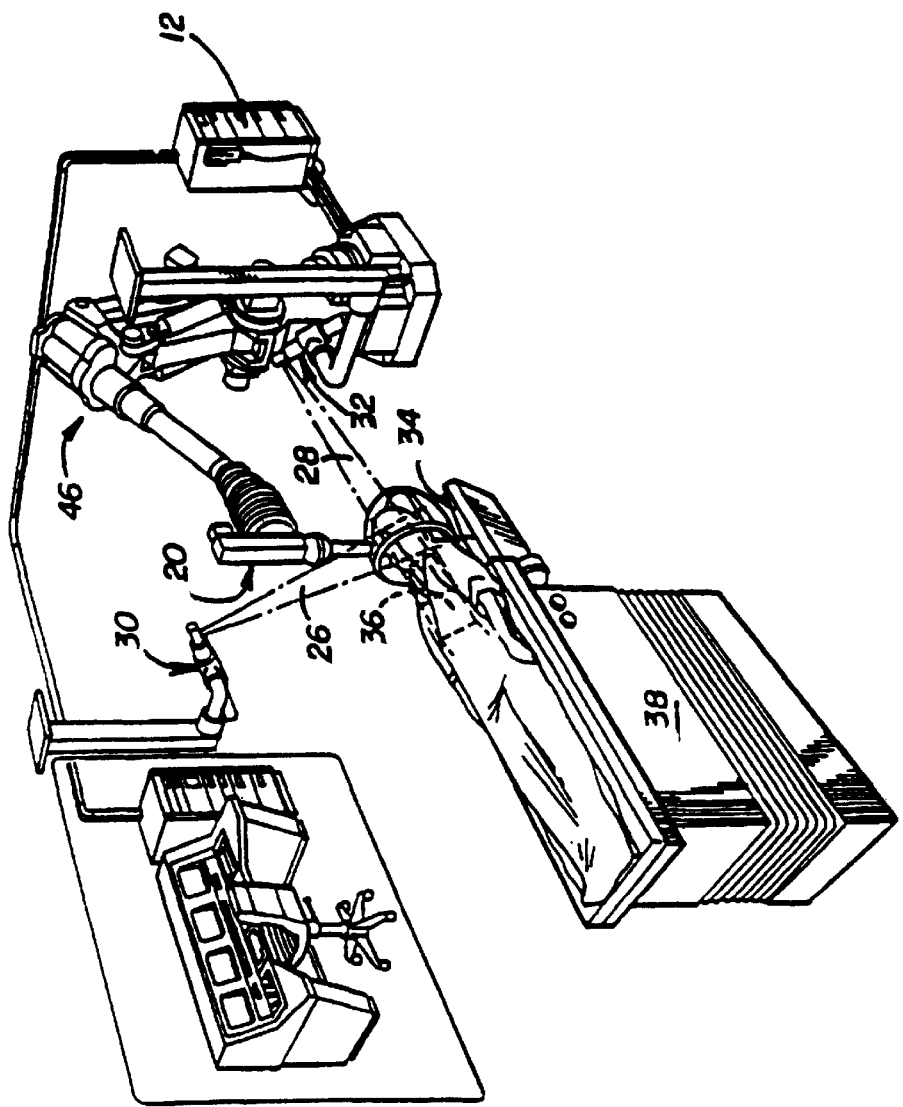
FIG. 3 is a diagram illustrating more details of the radiation treatment device.

The radiation treatment device 10 may also include a device for adjusting the relative positions of the beaming apparatus 20 and the patient 14 so that the ionizing beam is continuously focused on the target region 18. In the radiation treatment device shown in FIG. 1, the positions of the beaming apparatus and the patient may be altered with six degrees of freedom by a gantry 40 and a moveable operating table 38 with a tilting top 44. The positions of the beaming apparatus relative to the patient may also be accomplished by using a processor controllable robotic arm mechanism 46 as shown in FIG. 3 which has six axes of motion. The robotic arm mechanism permits the beaming apparatus to be moved freely about the patient's body including up, down, longitudinally along or laterally along the body of the patient.

Figure 4:
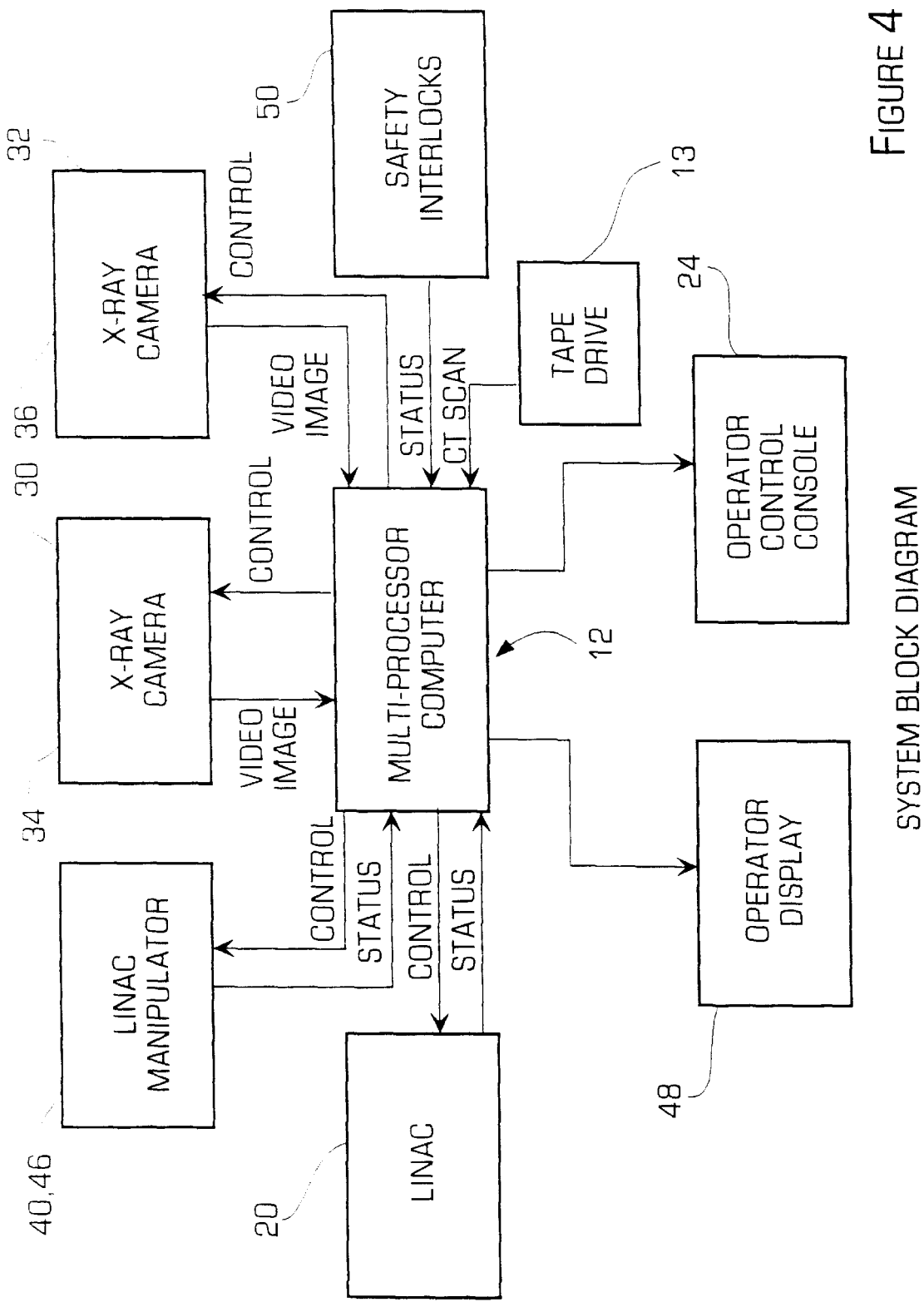
FIG. 4 is a block diagram illustrating the radiation treatment device.

FIG. 4 is a block diagram of the radiation treatment device 10 including the microprocessor 12, the tape drive 13, the beaming apparatus 20, the robotic arm 46 or the gantry 40, the x-ray cameras 30, 32, 34 and 36, and the operator control console 24 as described above. In addition, the device 10 may include safety interlocks 50 to ensure that the beaming apparatus is not activated accidentally. The device 10 may also include an operator display 48 for tracking the progress of the treatment and controlling the treatment. Any further details of the radiosurgery device may be found in U.S. Pat. No. 5,207,223 which is owned by the assignee of this application and which is incorporated herein by reference.

To accurately target the area to be irradiated in radiation therapy or radiosurgery, it is necessary to determine with high precision where the target is located during treatment. The above radiosurgery device may be ideally used for the treatment of brain or head tumors since the brain is fixed with respect to a rigid skull. The radiosurgery device may also be used with other fixed target regions in which it is easy to ensure that the ionizing beam strikes the target region, but not surrounding healthy tissue. If the target is adjacent to the diaphragm, however, the target will move during treatment due to breathing of the patient. The lung and other organs will move when the patient breaths or whenever the patient moves during the treatment. Therefore, it is desirable to provide an apparatus and method that follows a moving target region during a variety of different treatments, including radiation treatment. The apparatus may compensate for movements of the target region caused by breathing of the patient as well as movement of the target region caused by other movements of the patient.

In accordance with the invention, to determine the position of an internal moving target region such as an internal organ, external and internal markers (landmarks) may be used, as described below, and a model of their relative motions based on a series of images is determined prior to treatment. During treatment, little information is available on the placement of the internal landmarks except when the internal markers are periodically imaged using invasive devices, such as x-rays. However, the position of the external markers or a video image of the chest and/or abdomen may be determined with high precision and speed. Similarly, external sensors can provide measurement data is real time, i.e., at very high speed. Thus, the position of the external landmarks may be used in real time during treatment by inferring the placement of the internal (exact) markers by referencing the pre-operative model of the relative motion of internal and external markers. For verification, the placement of the internal markers can be determined periodically during treatment. An apparatus that compensates for breathing and other patient motion in accordance with the invention will now be described.

Figure 5:
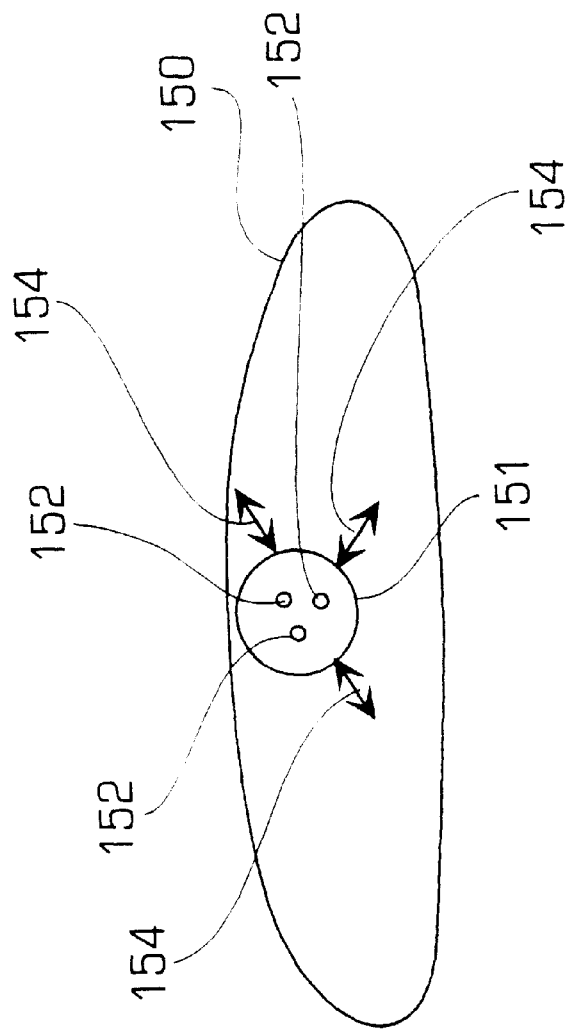
FIG. 5 is a diagram illustrating internal markers on a target organ moving as the target organ moves.

FIG. 5 is a diagram illustrating a set of internal markers 152 in accordance with the invention placed on a target organ 151 within a body 150 of the patient. The moving target organ 151 may be, for example, an organ near the diaphragm such as a lung or a liver which may move as the patient moves or as the patient inhales or exhales. In accordance with the invention, it is desirable to be able to track the motion of the target organ so that the treatment, such as ionizing radiation, is applied to the target organ and not to the healthy surrounding tissue. To track the movement of the target organ 151, the one or more internal markers 152 may be attached to various locations on the target organ 151. Then, as the target organ moves, the internal markers also move as shown by arrows 154. From the movement of the internal markers, it is possible to precisely determine the position of the target organ. In a preferred embodiment, more than one internal marker may be used in order to measure the movement of different areas of the target organ and the internal markers may be made of gold so that, although the internal markers are not visible outside of the body, the internal markers may be viewed using an imaging technique, which may preferably be stereotaxic x-ray imaging, but may also be ultrasound.

FIG. 6 is a diagram illustrating one or more internal markers 152 attached to the target organ 151 being imaged by a stereotaxic x-ray device. As shown in FIG. 6, the internal markers 152 on the target organ 151 may be imaged by a first x-ray source 160 and a second x-ray source 162 which are positioned at some predetermined angle with respect to each other similar to the diagnostic x-ray beams shown in FIGS. 1–3. The x-ray sources may generate a first and second diagnostic x-ray beam 164, 166 which pass through the target organ 151 near the internal markers 152 and are received by a first and second x-ray receiver 168, 170, respectively, which receive the x-ray beams and generate an electrical signal corresponding to the received x-rays. The stereotaxic x-ray device permits the precise location of the internal markers 152 to be determined by analyzing the images generated.

Figure 7B:
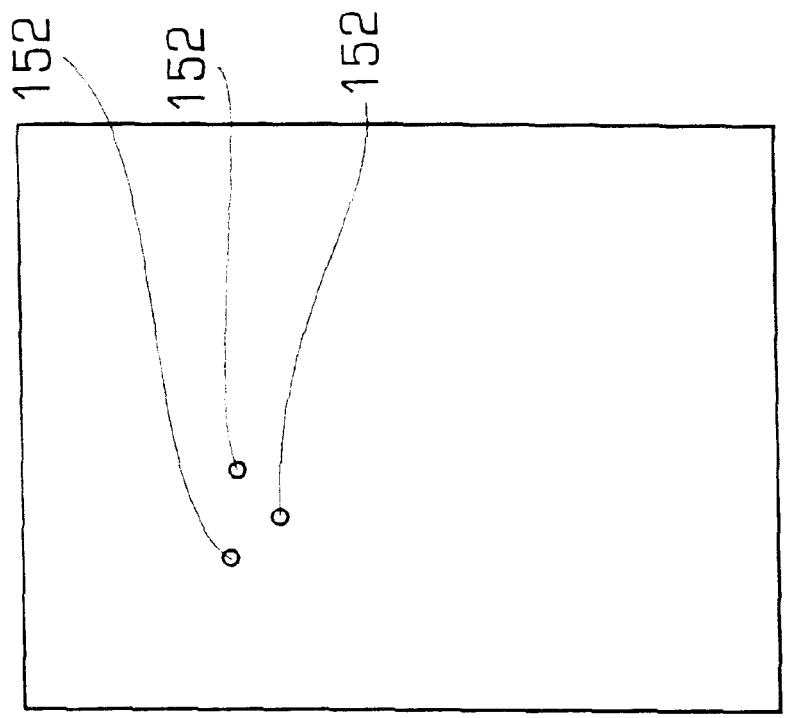
FIGS. 7A–7D are diagrams illustrating the imaging of the internal markers in accordance with the invention.
Figure 7A:
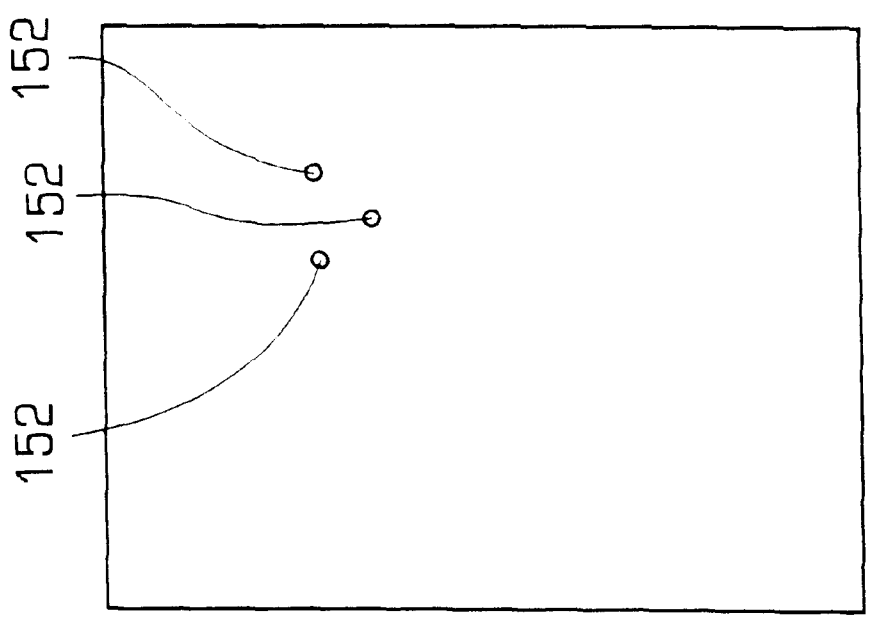
Figure 7D:
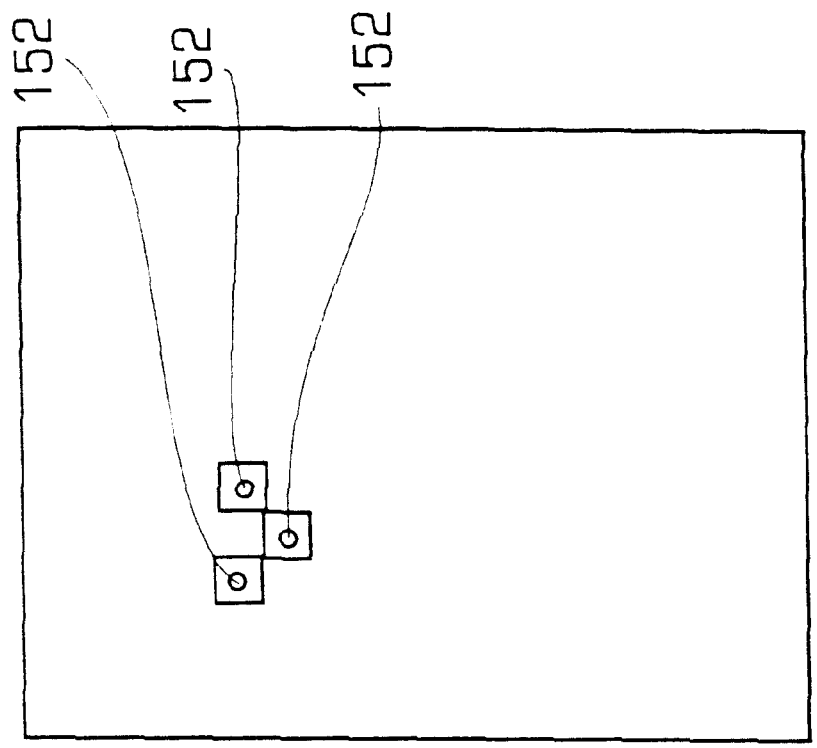
Figure 7C:
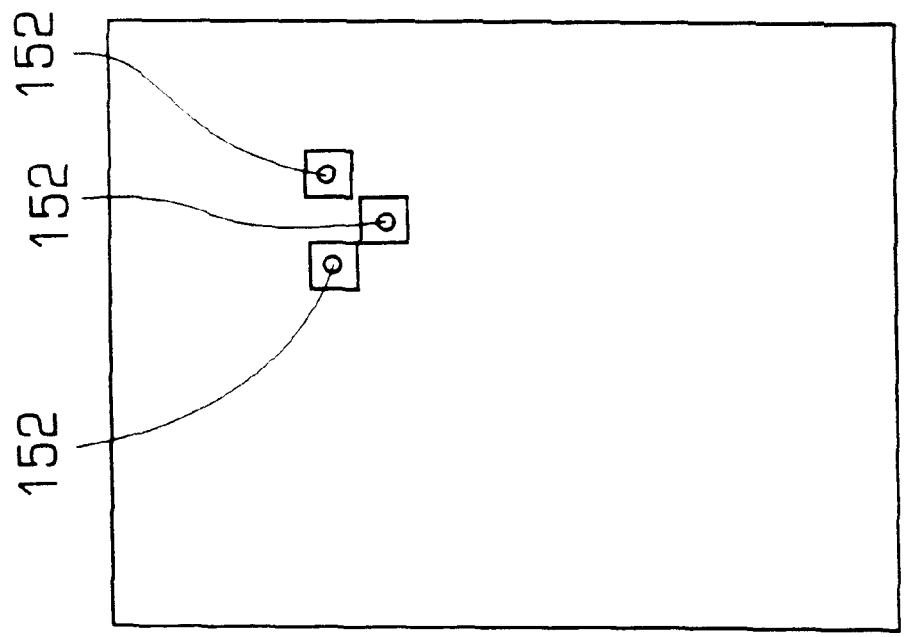

FIGS. 7A–7D are diagrams illustrating examples of the x-ray images of a target organ that include the internal markers 152 in accordance with the invention. FIGS. 7A and 7C show the same x-ray image with the internal markers 152 unenhanced and with the internal markers 152 being computer enhanced, respectively. Similarly, FIGS. 7B and 7D also illustrate the same x-ray image with unenhanced internal markers and computer enhanced internal markers, respectively. Thus, the stereotaxic x-ray imaging permits the precise location of the internal markers to be determined. The problem is that, using the stereotaxic x-ray device, internal marker positions may be determined only at predetermined intervals during treatment. In particular, the interval between imaging of the internal markers is necessary in order to limit the patient's exposure to the radiation and because the treatment beam can not be activated while the x-ray diagnostic imaging occurs. However, determining the exact position of the target organ periodically is not sufficient in order to accurately compensate for breathing and other motions of the patient. Therefore, one or more external markers may be placed on the skin of the patient near the target organ in accordance with the invention as will be described with reference to FIG. 8. As an alternative to external markers, the current state of respiration may be measured by viewing video images of the chest and/or abdomen movement.

Figure 8:
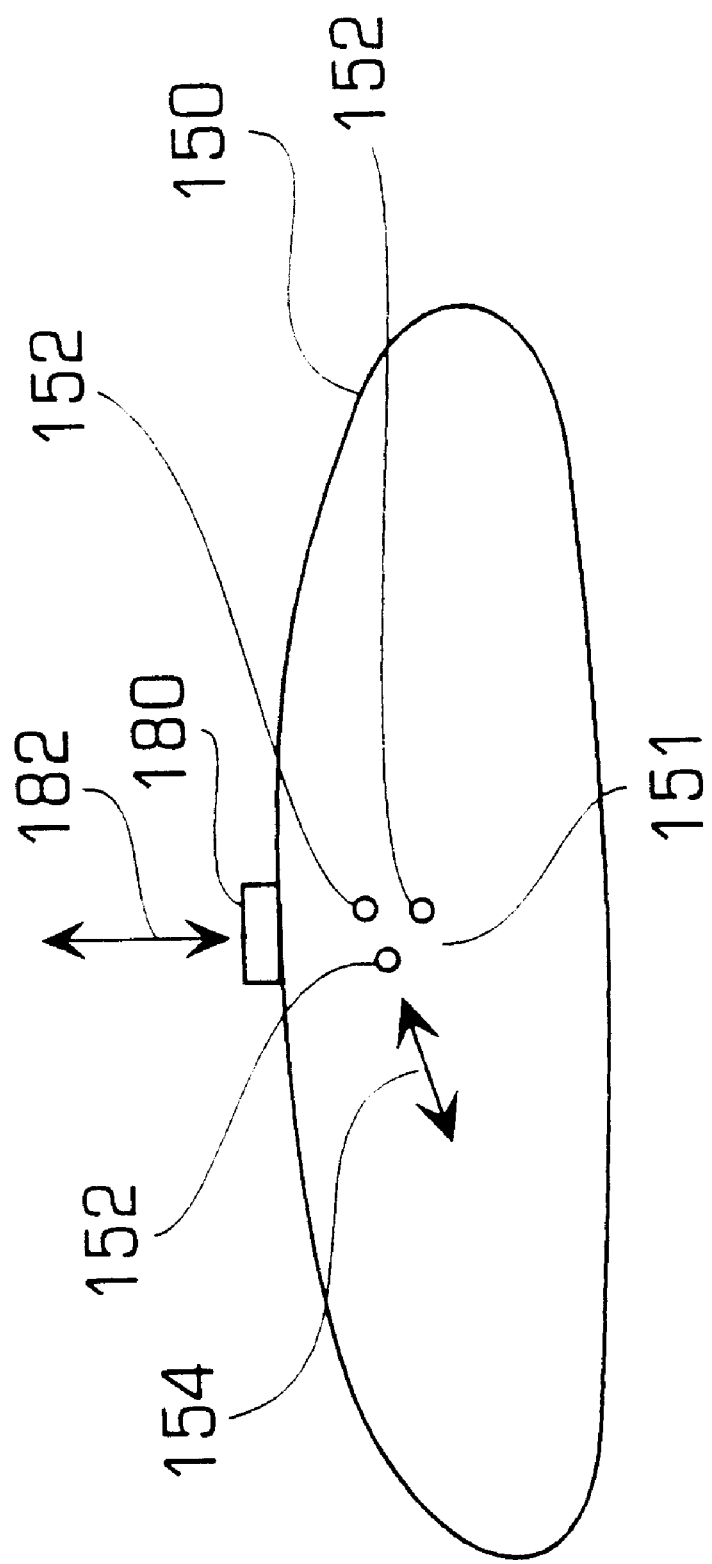
FIG. 8 is a diagram illustrating the internal markers in combination with an external marker to track the motion of the target region in accordance with the invention.

FIG. 8 is a diagram illustrating the target organ 151 within a patient's body 150 having internal markers 152 in combination with one or more external markers 180 attached to the skin of the patient in accordance with the invention. The one or more external markers 180 that are attached to the skin of the patient permit the motion 182 of the abdomen or chest wall to be determined. In the example of the breathing of a patient, the external marker may track the external motion as the patient inhales and exhales. The external markers 180 may be automatically tracked with a number of optical methods, such as infrared or visible light, and the position of the external marker may be determined more than 60 times per second. The external markers may also be attached to a belt, a flexible ring or a vest which fits around the waist of the patient.

If only external markers are used to compensate for the motion of the patient, however, they cannot accurately reflect the internal motion of the target organ since the target organ may move a small amount while the external marker may move a larger amount and vice versa. The external markers are not sufficiently precise to compensate for the motion of the patient. Therefore, the combination of the internal markers and the external markers is necessary in order to accurately track the motion of the target organ. Thus, the periodic x-ray imaging of the internal markers is synchronized with the continuous optical tracking of the external markers to provide accurate tracking of the motion of the target organ. In order to synchronize the motion of the internal and external markers, it is necessary to determine the relationship between the positions of the internal and external markers which may occur at the start of the treatment process and will be described below with reference to FIG. 10.

When some movement of the target organ is detected, the treatment system, such as the radiosurgery device described above, may compensate for the movement in a number of different ways. For example, the treatment system may move the treatment device, such as the beaming apparatus 20, relative to the patient or vice versa. The treatment system may also move a shaping or collimating device into the path of the treatment device to change the characteristics of the treatment device. The treatment system may also only activate the treatment device when the target organ is within the treatment path or block the treatment device when the target organ is not within the treatment path. Now, one of the benefits of the motion compensation apparatus in accordance with the invention will be illustrated and described.

Figure 9B:
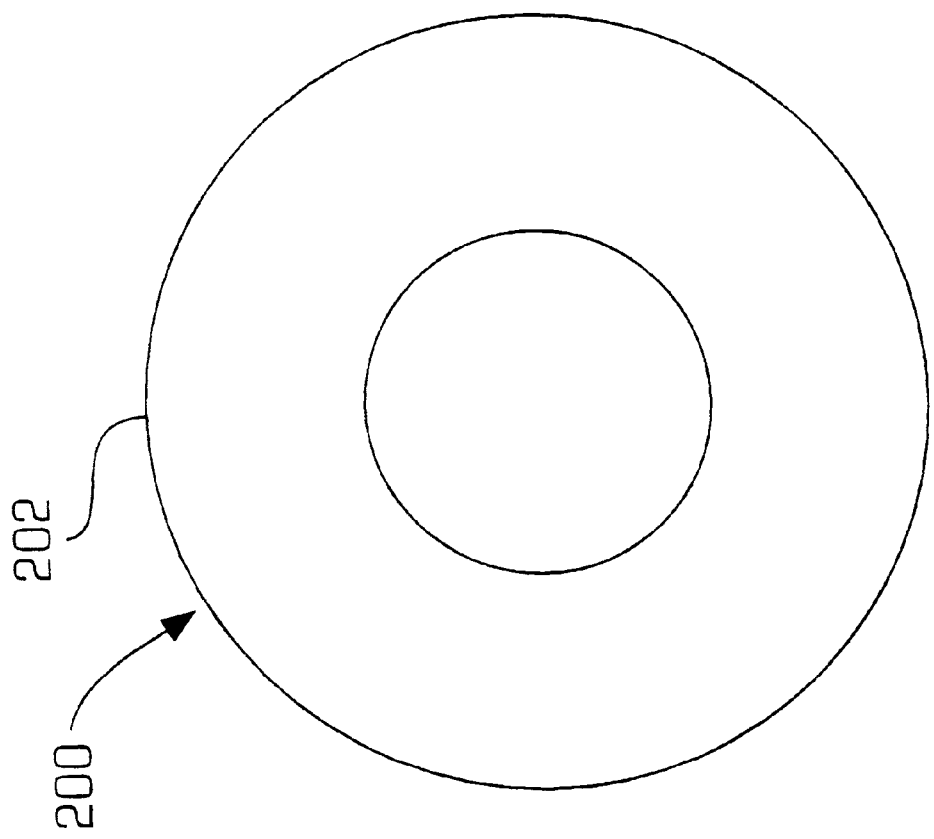
FIGS. 9A–9D are diagrams illustrating the reduction in the safety seam in accordance with the invention.
Figure 9A:
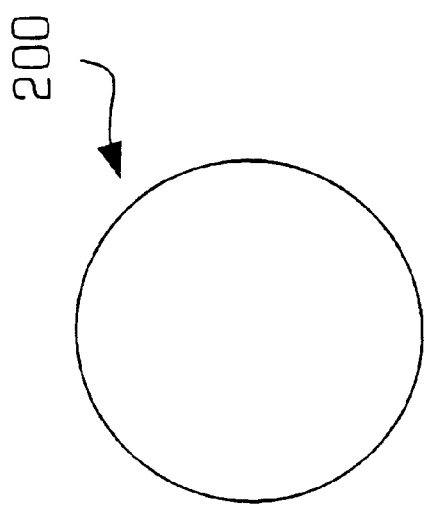
Figure 9D:
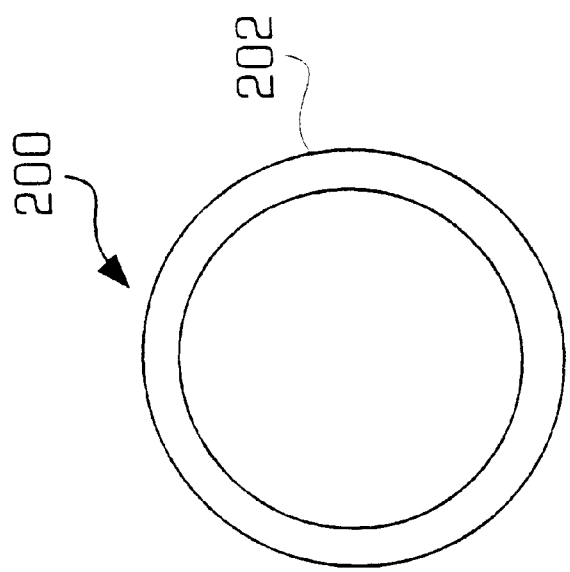
Figure 9C:
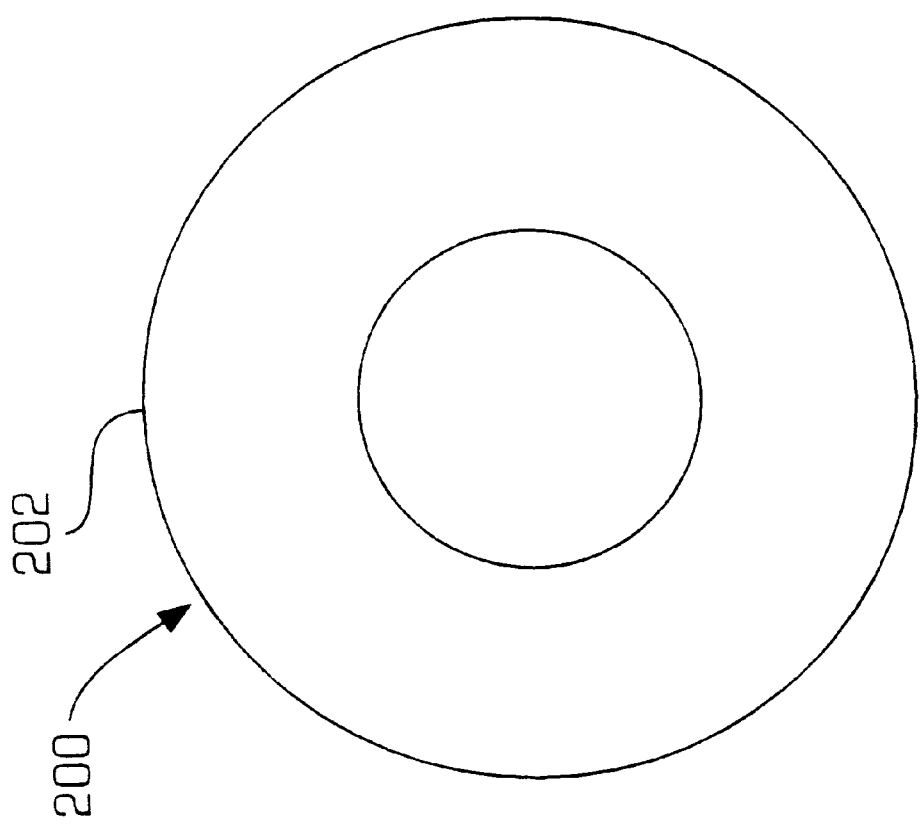

FIGS. 9A–9D are diagrams illustrating one benefit of the motion compensation apparatus in accordance with the invention. In particular, FIG. 9A shows a volume of be treated 200 without a safety seam. In particular, the volume may have no safety seam provided that the position of the target region to be treated is precisely known so that healthy tissue is not damaged. If the position of the target region cannot be exactly determined, such as for a moving target organ due to breathing and other patient motion, the volume 200 requires a safety seam 202 as shown in FIG. 9B. The problem with the safety seam is that the required radiation dose increases very rapidly with the diameter of the target. For example, for a spherical target the ratio between the diameter of the target and the required dose is cubic. The safety seam 202 for a typical radiosurgery device is shown in FIG. 9C. FIG. 9D shows the much reduced safety seam 202 which is possible due to the motion compensation apparatus and method in accordance with the invention. A reduction of the safety seam by a factor of two results in a volume reduction of the dose by a factor of eight. Thus, the unwanted dose to healthy tissue may be reduced by a factor of four while the dose to the target organ or tumor may be doubled. For a large variety of cancer cases with particularly grim prognosis, the motion compensation apparatus in combination with typical radiosurgery devices can greatly improve the efficacy of the treatment. Now, a method for motion compensation during treatment in accordance with the invention will be described.

Figure 10:
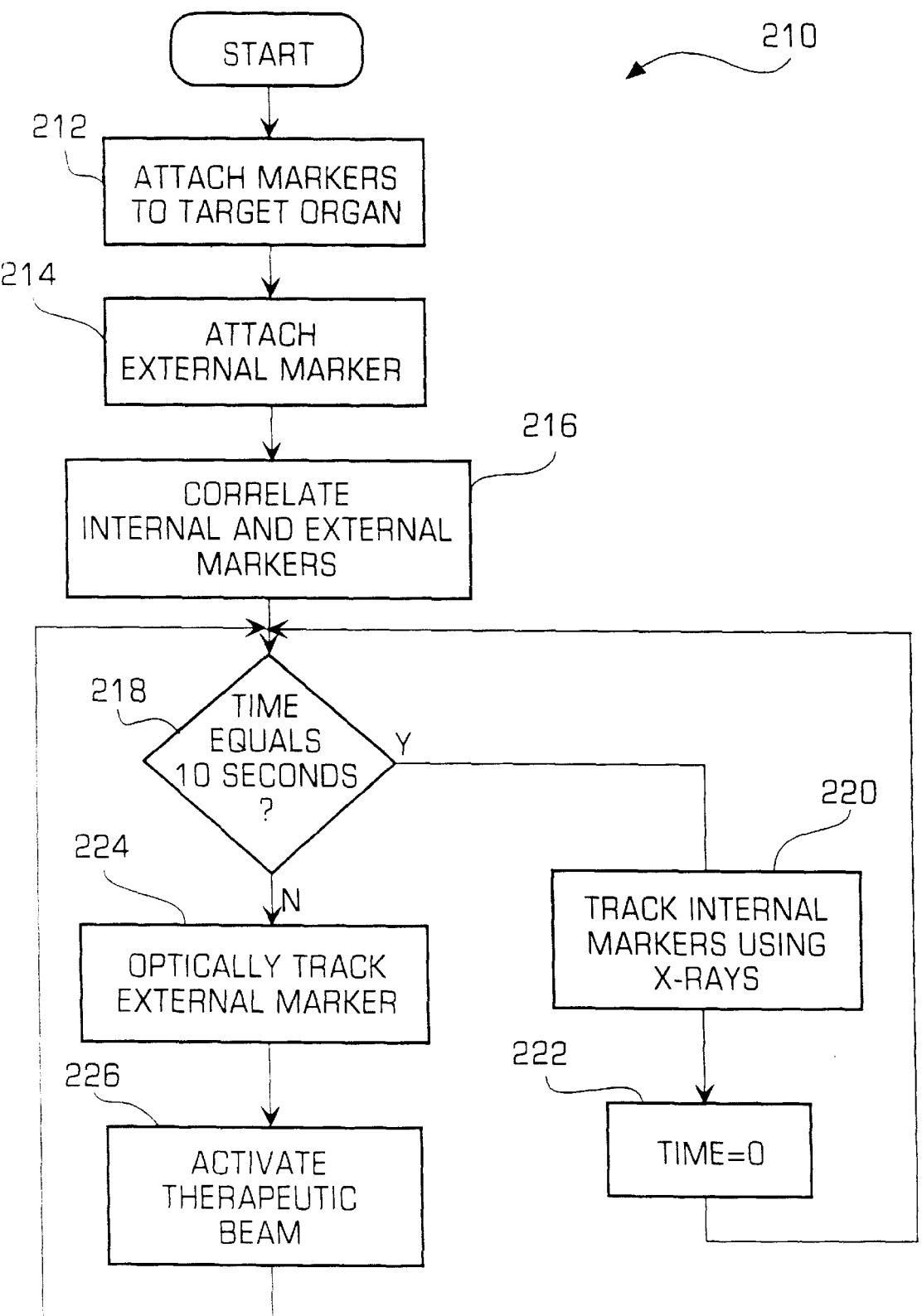
FIG. 10 is a flowchart illustrating a method for compensating for breathing and other motion in a radiosurgical device.

FIG. 10 is a flowchart illustrating a method 210 for compensating for breathing and other motion of a patient during treatment, such as with a radiosurgical device. The first few steps in the method may be performed at a time prior to the actual treatment of the patient. In particular, a surgeon may attach a set of internal markers in the proximity of or within the target organ during a short surgical procedure in step 212 and then, just prior to treatment, the surgeon may attach a set of external markers to the chest or abdominal wall of the patient near the target organ in step 214. Next, the processor of the radiosurgery device correlates the position of the internal markers and the external markers in step 216 just prior to starting the treatment of the patient. The method for correlating the internal markers with the external markers is described below with reference to FIG. 11. Once the positions of the internal and external markers have been correlated, the treatment of the patient may begin. The next steps of the method occur during the treatment of the patient.

First, the apparatus determines if the total elapsed time since the last time the internal markers were imaged is equal to a predetermined number of seconds. The predetermined number of seconds is preferably between two and ten seconds and more preferably about ten seconds. If the total elapsed time is equal to the predetermined number of seconds, then the treatment beam is deactivated and the internal markers are imaged using, for example, stereotaxic x-ray imaging in step 220. Next, the total elapsed time is reset to zero and the method returns to step 218. Thus, in accordance with the invention, the internal markers are imaged every predetermined number of seconds. Returning to step 218, if the total elapsed time is not equal to the predetermined number of seconds, then the external markers are optically tracked in step 224 while the treatment beam is activated in step 226. The external markers may be tracked so that position data is provided to the processor of the radiosurgery device as much as sixty times per second. The processor may then correlate the position of the external markers with the internal markers and generate positional data about any change in the position of the target organ. Thus, between the periodic imaging of the internal markers, the position of the external markers is used to track the position of the target.

When some movement of the target organ is detected, the treatment system, such as the radiosurgery device described above, may compensate for the movement in a number of different ways. For example, the treatment system may move the treatment device, such as the beaming apparatus 20, relative to the patient or vice versa. The treatment system may also move a shaping or collimating device into the path of the treatment device to change the characteristics of the treatment device. The treatment system may also only activate the treatment device when the target organ is within the treatment path or block the treatment device when the target organ is not within the treatment path. Now, a method for correlating the positions of the internal and external markers in accordance with the invention will be described.

Figure 11:
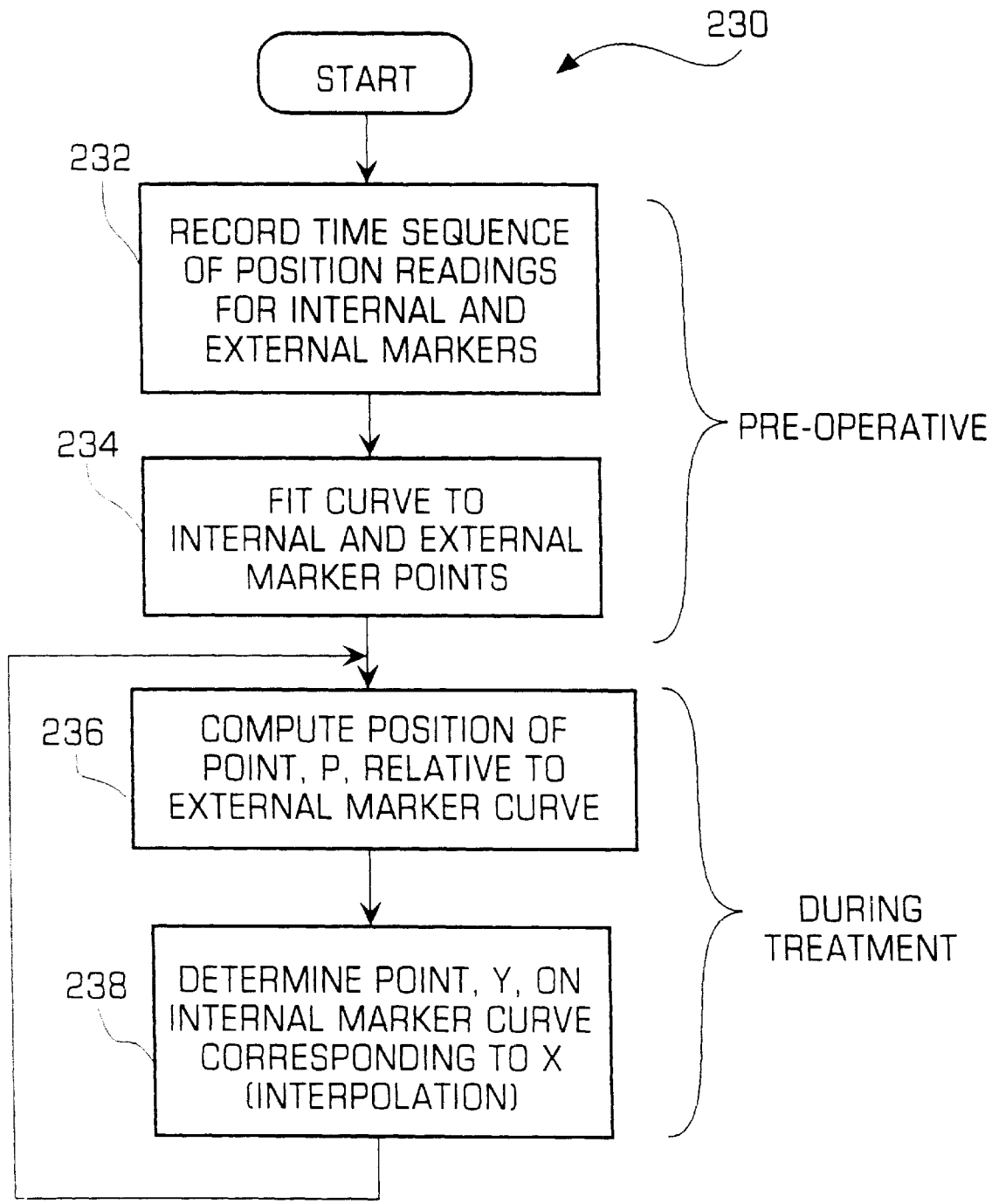
FIG. 11 is a flowchart illustrating a method for correlating the internal and external markers in accordance with the invention.

FIG. 11 is a flowchart illustrating a method 230 for correlating the positions of the internal and external markers in accordance with the invention. Several steps of the method occur during the pre-operative process while several steps occur during the actual treatment. In particular, in step 232, a series of time sequence images are generated for both the internal and external markers throughout the respiratory cycle so that a plurality of points corresponding to the internal and external markers are generated during the pre-operative phase. The plurality of points corresponding to the external markers and the internal markers may each be referred to as a point cloud. Next, the processor in the radiosurgery device may fit a curve to the points generated for the internal markers and a separate curve to the points generated by the external markers in step 234. These curves permit the positions of the external and internal markers to be correlated to each other.

During the actual treatment, the system generates a position, x, of the external markers by a technique, such as infrared imaging, at a particular time and that position, x, is fit to the previously generated curve of the external marker positions in step 236. Next, in step 238, a position, y, of a point on the internal marker curve which corresponds to the position, x, is determined by comparing the two curves which is a process known as interpolation. This process may be performed for each marker. Using this method, the position of the external markers may be correlated to the position of the internal markers which permits the system to accurately determine the amount of movement of the target organ without actually imaging the internal organ. Another way to perform the correlation of the positions of the internal and external markers is to use a neural network trained to perform interpolation or other known mathematical interpolation methods for establishing the correspondence between the internal and external markers after having computed the point clouds.

Now, four different embodiments of the method for compensating for breathing and other patient motion in accordance with the invention will be described. In all of these embodiments, the respiratory and diaphragmatic excursion may be limited and minimized by binding the abdomen or compressing the abdomen. In a first embodiment, one or more small metal markers (also known as landmarks) are attached to the target organ before treatment. There may be three or four metal markers with possibly distinct shapes or sizes, which may be, for example, small gold beads. The exact position of these internal markers is determined by two x-ray cameras, which acquire a stereo image of the target site. There may also be one or more infra-red probes which are attached to the patient's skin surface. The infra-red probes give a very accurate and high speed position reading, but they only show the surface of the patient's body. In this embodiment, internal imaging of the internal markers and external imaging of the external markers (i.e., x-ray imaging and infrared imaging) are combined. In particular, prior to treatment, a series of images with both modalities (i.e., x-ray and infrared, respectively) is obtained. For these images, the time of image acquisitions is recorded, or at least the images with both modalities are acquired simultaneously so that the time of image acquisition does not vary by more than approximately 0.01 sec. In this way, a series of pre-operative images of both external and internal landmarks is acquired where each image has a time-stamp. These series of images determines a model of the relative motion between internal and external landmarks as described above.

During the actual operation, it is difficult to obtain x-ray images more than once every predetermined number of seconds due to concerns about exposing the patient to too much radiation and due to the fact that the treatment beam cannot operate when x-ray imaging is being done. The x-ray imaging alone would therefore be too slow to follow breathing motion with high precision. Therefore, the external landmarks on the skin surface, as seen by the infrared system, are used for intra-operative localization, where we continuously reference the previously computed model of relative motions of the internal and external markers. This allows the exact placement of the internal landmarks (gold beads) to be predicted at time points where no x-ray images are available. Now, a second embodiment of the method will be described.

In a second embodiment of the method in accordance with the invention, no internal landmarks attached to the target organ are used. Instead, an ultra-sound camera is used to acquire the pre-operative image series, again in combination with an infra-red tracking system. The infra-red system in this embodiment establishes both the position of the external landmarks and the position of the (movable) ultra-sound camera, which must be moved by a human operator during this pre-operative phase. During the pre-operative phase, the ultra-sound images may be analyzed manually or semi-automatically in order to locate the target. During treatment, the external landmarks (infra-red probes) are used to compensate for the motion of the target organ since the motion model we have established allows the determination of the position of the internal target organ from the position of the external markers. Now, a third embodiment of the method will be described.

A third embodiment is very similar to the second embodiment except that a device for measuring the air flow may be used instead of the ultrasound camera. The device may be a mouthpiece that records the direction and volume of airflow and correlates these measurements with the location of the internal fiducials or any other mechanism for detecting the location of the internal organs. In this embodiment, a reference position of the target organ, such as a lung, such as at full exhalation or at full inhalation or any intermediate respiratory state may be used to correlate the current respiratory state to a state imaged prior to the treatment so that the motion and position of the target organ may be determined during the treatment and the position of the treatment device may be moved based on the determined motion of the target organ. Now, a fourth embodiment of the invention will be described.

In a fourth embodiment of the invention, a slightly different technique is used. In particular, during most radiation treatments, the patient is awake and conscious so that it is often difficult to determine whether a motion observed by real-time tracking of external markers is indeed due to breathing and not to other small movements of the patient's body. Such other movements of the body may be caused, for example, by sneezing or other sudden motions. To detect and accurately track these other motions, a pair of x-ray cameras in addition to the ultrasound camera described above may be used. In this embodiment, the ultra-sound camera is only used before the operation to determine the correlation between the target motion and the motion of external landmarks as described above. Thus, a series of pre-operative images is again acquired to determine the relationship between the motion of the patient's skin surface and the target organ. During treatment, the x-ray cameras may be used to determine sudden motion of the patient based on well known computer methods for automatically finding bony landmarks in x-ray images. These x-ray images may be compared to pre-operative tomographic images (CT or MR images) to determine sudden movement of the patient.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. An apparatus for compensating for breathing and other motions of the patient during treatment, the apparatus comprising:
   a first detection device for periodically generating positional data about a target region internal to the body of the patient;
   a second detection device for continuously generating positional data about one or more sensors external to the body of the patient; and
   a processor that receives the periodic positional data about the internal target region and the continuous position data from the external sensors in order to generate a correspondence between the position of the internal target region and the external sensors so that the treatment is directed towards the position of the internal target region of the patient based on the positional data obtained from the external sensors to compensate for motions of the patient.

2. The apparatus of claim 1, wherein the first detection device comprises one or more markers adapted to be attached to the internal target region within the patient's body and an imaging device for imaging the markers within the patient's body.

3. The apparatus of claim 2, wherein the imaging device comprises a stereotaxic x-ray device.

4. The apparatus of claim 3, wherein the one or more markers comprise metal beads adapted to be attached to the internal target region.

5. The apparatus of claim 1, wherein the first detection device comprises an ultrasound device for imaging the internal target region prior to treatment.

6. The apparatus of claim 5, wherein the first detection device further comprises an imaging device for detecting movement of the patient during the treatment.

7. The apparatus of claim 6, wherein the imaging device comprises a stereotaxic x-ray device.

8. The apparatus of claim 1, wherein the second detection device comprises one or more infrared markers adapted to be attached to the body of the patient and an infrared imaging device for imaging the infrared markers.

9. The apparatus of claim 1, wherein the second detection device comprises a visible imaging device.

10. The apparatus of claim 1, wherein the second detection device comprises a flow meter that measures respiration of the patient.

11. The apparatus of claim 10, wherein the second detection device further comprises means for compressing the abdomen of the patient to limit respiratory motion.

12. The apparatus of claim 1, wherein the processor further comprises means for correlating the periodic positional data of the internal target region with the positional data of the external markers.

13. The apparatus of claim 1, wherein the treatment comprises radiation treatment.

14. The apparatus of claim 1, wherein the treatment comprises a biopsy needle.

15. The apparatus of claim 1, wherein the treatment comprises a laser beam treatment.

16. The apparatus of claim 1, wherein the treatment comprises a focused energy treatment including one of ablation and ultrasound.

17. The apparatus of claim 1, wherein the external markers comprises a device worn around the waist of the user with the one or more external markers attached to the device, the device comprising one of a belt, ring and vest.

18. The apparatus of claim 1 further comprising means for altering the treatment in response to changes in the position of the target region.

19. The apparatus of claim 18, wherein the altering means comprises means for moving the treatment relative to the patient.

20. The apparatus of claim 18, wherein the altering means comprises means for changing the characteristics of the treatment.

21. The apparatus of claim 20, wherein the changing means comprises means for collimating the treatment beam.

22. The apparatus of claim 20, wherein the changing means comprises means for blocking the treatment beam at predetermined times.

23. A method for compensating for breathing and other motions of the patient during treatment, the method comprising:

periodically generating positional data about a target region internal to the body of the patient;

continuously generating positional data about external motion of the patient's body using one or more external sensors; and generating a correspondence between the position of the internal target region and the external sensors so that the treatment is directed towards the position of the internal target region of the patient based on the positional data of the external sensors to compensate for motions of the patient.

24. The method of claim 23, wherein periodically generating positional data comprises attaching one or more markers adapted to be attached to the internal target region within the patient's body and imaging the markers within the patient's body.

25. The method of claim 24, wherein the imaging comprises generating a stereotaxic x-ray image of the patient.

26. The method of claim 23, wherein generating the periodic positional data comprises imaging the internal target region with an ultrasound device prior to treatment.

27. The method of claim 26, wherein generating the positional data prior to treatment further comprises detecting movement of the patient during the treatment.

28. The method of claim 23, wherein generating the positions of the external markers comprises attaching one or more infrared markers adapted to be attached to the patient and imaging the infrared markers with an infrared imaging device.

29. The method of claim 23 further comprising binding the patient to reduce respiratory motion, and wherein the external sensor comprises a flow meter that measures respiration.

30. The method of claim 23, wherein generating the correspondence further comprises correlating the periodic positional data of the internal target region with the positional data of the external sensors.

31. The method of claim 23, wherein the treatment comprises radiation treatment.

32. The method of claim 23, wherein the treatment comprises a biopsy needle.

33. The method of claim 23, wherein the treatment comprises a laser beam treatment.

34. The method of claim 23, wherein the treatment comprises a focused energy treatment including one of ablation and ultrasound.

35. The method of claim 23, wherein attaching the external markers comprises attaching a device adapted to be attached to the patient having one or more external markers attached to the device, the device comprising one or a belt, a ring and a vest.

36. The method of claim 23 further comprising altering the treatment in response to changes in the position of the target region.

37. The method of claim 36, wherein the altering comprises moving the treatment relative to the patient.

38. The method of claim 36, wherein the altering comprises changing the characteristics of the treatment.

39. The method of claim 38, wherein the changing comprises collimating the treatment beam.

40. The method of claim 38, wherein the changing comprises blocking the treatment beam at predetermined times.

41. An apparatus for performing a treatment on an internal target region while compensating for breathing and other motions of the patient, the apparatus comprising:

a first imaging device for periodically generating positional data about a target region internal to the body of the patient;

a second imaging device for continuously generating positional data about one or more external sensors attached to the patient's body;

a processor that receives the positional data about the internal target region and the external sensors in order to generate a correspondence between the position of the internal target region and the external sensory data to compensate for motions of the patient; and a treatment device that directs the treatment towards the position of the internal target region of the patient based on the data of the external sensors.

42. An apparatus for compensating for breathing and other motions of the patient during treatment, the apparatus comprising:

a first detection device for periodically generating positional data about a target region internal to the body of the patient;

a second detection device for continuously generating positional data about one or more external markers showing external motion of the patient's body when the first imaging device is not active; and a processor that determines the position of the internal target region to be treated when the first imaging device is not active to compensate for motions of the patient, the position being determined based on the generated position of the external markers which corresponds to a predetermined position of the internal target region.

* * * * *